US005772580A

United States Patent [19]
Utsui et al.

[11] Patent Number: 5,772,580
[45] Date of Patent: Jun. 30, 1998

[54] BIOLOGICAL FLUORESCENCE DIAGNOSTIC APPARATUS WITH DISTINCT PICKUP CAMERAS

[75] Inventors: Tetsuya Utsui; Hiroshi Sano; Rensuke Adachi, all of Tokyo, Japan

[73] Assignee: Asahi Kogaku Kogyo Kabushiki Kaisha, Tokyo, Japan

[21] Appl. No.: 607,361

[22] Filed: Feb. 27, 1996

[30] Foreign Application Priority Data

Mar. 3, 1995 [JP] Japan .................................. 7-043782
Oct. 6, 1995 [JP] Japan .................................. 7-259948
Oct. 31, 1995 [JP] Japan .................................. 7-282905

[51] Int. Cl.⁶ ...................................................... A61B 1/04
[52] U.S. Cl. .......................... 600/160; 600/113; 600/181; 600/478
[58] Field of Search .................................... 600/109, 118, 600/172, 173, 112, 113, 178, 160, 310, 476, 478, 342; 128/653.1, 633, 634, 664, 665

[56] References Cited

U.S. PATENT DOCUMENTS

| | | |
|---|---|---|
| 4,676,593 | 6/1987 | Adachi et al. . |
| 4,768,513 | 9/1988 | Suzuki ..................................... 128/634 |
| 4,821,117 | 4/1989 | Sekiguchi ............................ 600/178 X |
| 4,942,867 | 7/1990 | Takahashi et al. . |
| 5,049,910 | 9/1991 | Hsiung ..................................... 354/210 |
| 5,078,503 | 1/1992 | Ueda . |
| 5,105,269 | 4/1992 | Nakamura et al. ................. 600/109 X |
| 5,239,983 | 8/1993 | Katsurada . |
| 5,445,157 | 8/1995 | Adachi et al. . |
| 5,507,287 | 4/1996 | Palcic et al. ............................ 128/633 |

FOREIGN PATENT DOCUMENTS

| | | |
|---|---|---|
| 0512965 | 5/1992 | European Pat. Off. . |
| 654792 | 9/1994 | Japan . |

*Primary Examiner*—John P. Leubecker
*Attorney, Agent, or Firm*—Greenblum & Bernstein P.L.C.

[57] ABSTRACT

A biological fluorescence diagnostic apparatus having a device for irradiating a biological tissue with light which excites the tissue to generate fluorescent light, and a device for taking a fluorescence image of the biological tissue passing through an ocular optical system of an endoscope. The apparatus further has a television camera unit including a television camera for taking an ordinary endoscopic observation image passing through the ocular optical system, and a television camera with an image intensifier for taking a fluorescence observation image passing through the ocular optical system after amplifying the light intensity of the image. An optical path switching system which includes a reflective surface is selectively inserted and withdrawn from the optical path of light passing through the ocular optical system so as to selectively produce ordinary and fluorescence images in the television camera unit. A filter is selectively inserted into and movable out of an illuminating light path of the endoscope in response to detection of the position of the optical path switching system.

17 Claims, 5 Drawing Sheets

5,772,580

BIOLOGICAL FLUORESCENCE DIAGNOSTIC APPARATUS WITH DISTINCT PICKUP CAMERAS

BACKGROUND OF THE INVENTION

The present disclosure relates to subject matter contained in Japanese Patent Application No. 7-43782 (filed on Mar. 3, 1995), Japanese Patent Application No. 7-259948 (filed on Oct. 6, 1995) and Japanese Patent Application No. 7-282905 (filed on Oct. 31, 1995) which are expressly incorporated herein by reference in their entireties.

1. Field of the Invention

The present invention relates to a biological fluorescence diagnostic apparatus for making an early diagnosis of cancer or other diseases by fluorescence observation using an endoscope.

2. Description of the Prior Art

An endoscope that is used for fluorescence observation is the same as those which are used for ordinary endoscopic observation in which an observation image that is obtained by an objective optical system disposed in the distal end of an insert part is transmitted to an eyepiece through an image guide fiber bundle inserted in the insert part and observed through an ocular optical system.

When ordinary observation is to be made with such an endoscope, a television camera for ordinary observation is connected to the eyepiece; when fluorescence observation is to be made, the television camera is replaced by a television camera for fluorescence observation, which is equipped with an image intensifier.

However, it is extremely troublesome to change television cameras to be connected to the eyepiece every time the ordinary observation mode and the fluorescence observation mode are switched over from one to the other. Therefore, endoscopy, including fluorescence observation, cannot smoothly be carried out.

SUMMARY OF THE INVENTION

An object of the present invention is to provide an easy-to-use biological fluorescence diagnostic apparatus which is designed so that the ordinary observation mode and the fluorescence observation mode can be readily switched over from one to the other.

Other objects and advantages of the present invention will become apparent from the following detailed description of illustrated embodiments of the invention.

According to the present invention, there is provided a biological fluorescence diagnostic apparatus having a device for irradiating a biological tissue with illuminating light in a specific region of wavelengths at which the biological tissue generates fluorescent light upon light irradiation, and a device for taking a fluorescence image of the biological tissue passing through an ocular optical system of an endoscope. The biological fluorescence diagnostic apparatus includes a television camera unit having an ordinary image pickup television camera for taking an ordinary endoscopic observation image passing through the ocular optical system of the endoscope, and a fluorescence image pickup television camera with an image intensifier for taking a fluorescence observation image passing through the ocular optical system of the endoscope after amplifying the light intensity of the fluorescence observation image. The ordinary image pickup television camera and the fluorescence image pickup television camera are integral with each other. The apparatus further includes a device for operatively connecting the television camera unit to an eyepiece of the endoscope.

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENTS

Embodiments of the present invention will be described below with reference to the accompanying drawings.

Figure 1:
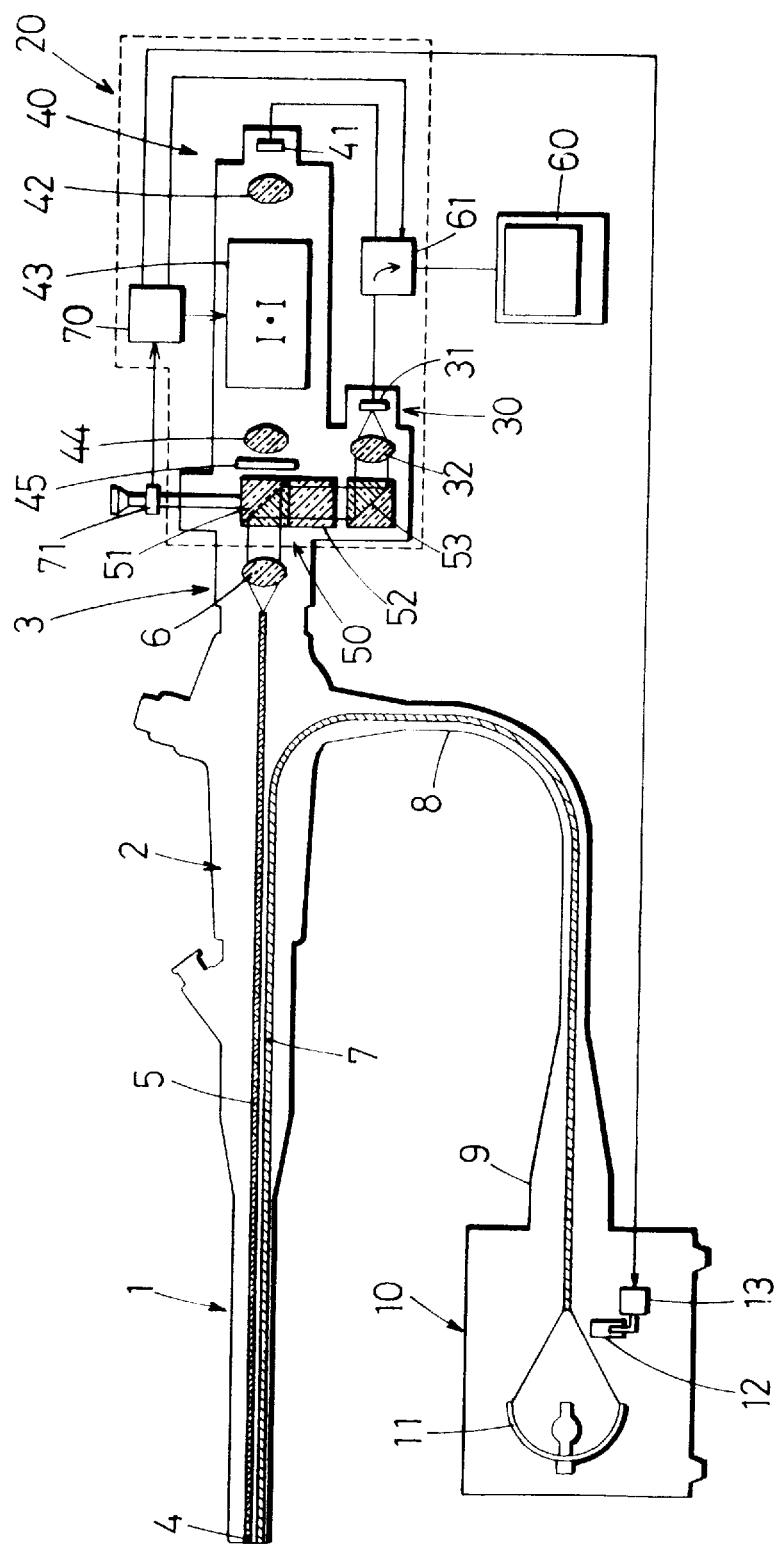
FIG. 1 shows the arrangement of a first embodiment of the present invention in an ordinary observation mode.

FIG. 1 shows a first embodiment of the present invention in a state where a television camera unit 20 is connected to an eyepiece 3 of an endoscope. The endoscope has an insert part 1 and a control part 2 which is connected to the proximal end of the insert part 1.

The distal end of the insert part 1 contains an objective optical system 4 for forming an image of an object on an entrance end surface of an image guide fiber bundle 5. The image guide fiber bundle 5 extends through the insert part 1 and the control part 2 so that an exit end surface of the image guide fiber bundle 5 reaches the eyepiece 3. The eyepiece 3 contains an ocular optical system 6 for observation of an enlarged image of the exit end surface of the image guide fiber bundle 5.

Accordingly, an image of an object lying in front of the distal end of the insert part 1 is formed by the objective optical system 4, and the image is transmitted to the eyepiece 3 through the image guide fiber bundle 5. When the television camera unit 20 is not connected to the eyepiece 3, the image of the object can be observed with the naked eye through the ocular optical system 6.

A light guide fiber bundle 7 for transmitting light for illuminating an object extends through the insert part 1 and the control part 2 and further extends through a light guide connecting tube 8. An exit end of the light guide fiber bundle 7 is disposed in parallel to the objective optical system 4. An entrance end of the light guide fiber bundle 7 is disposed in a connector 9 which is detachable with respect to a light source apparatus 10.

A light source lamp 11, which uses a xenon lamp, is disposed in the light source apparatus 10. Illuminating light emitted from the Light source lamp 11 is converged so as to enter the Light guide fiber bundle 7, and thus an object is illuminated by light emanating from the exit end of the light guide fiber bundle 7.

An exciting light filter 12 which transmits only light in a wavelength region of from about 420 nanometers to 480 nanometers is disposed in an illuminating light path between the light source lamp 11 and the entrance end of the light guide fiber bundle 7, such that the exciting light filter 12 can be selectively inserted into and withdrawn from the illuminating light path by the action of a solenoid 13.

Figure 2:
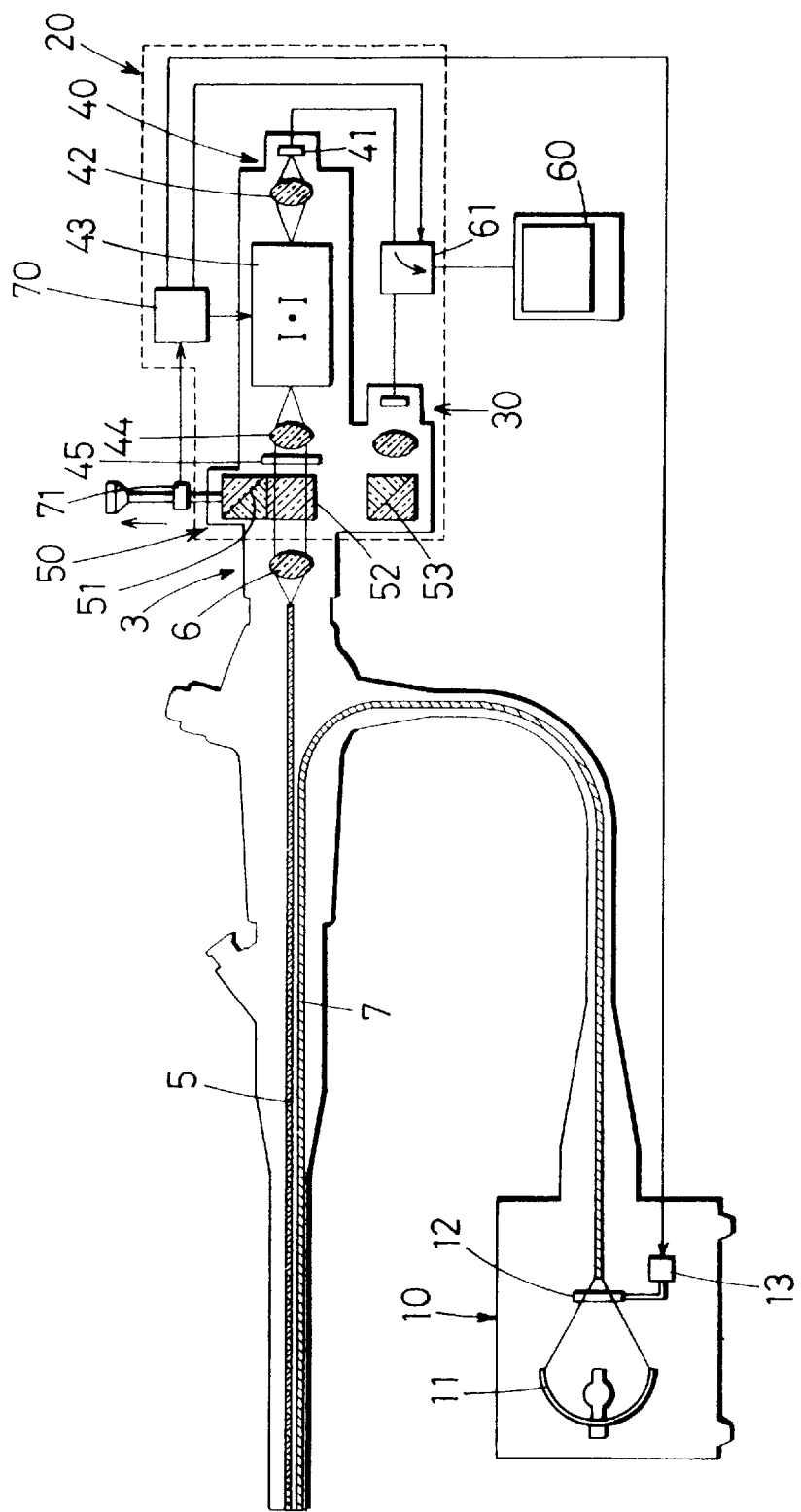
FIG. 2 shows the arrangement of the first embodiment of the present invention in a fluorescence observation mode.

When ordinary observation is to be made, the exciting light filter 12 is withdrawn from the illuminating light path, as shown in FIG. 1, When fluorescence observation is to be made, the exciting light filter 12 is inserted into the illuminating tight path, as shown in FIG. 2 (described later).

Figure 3:
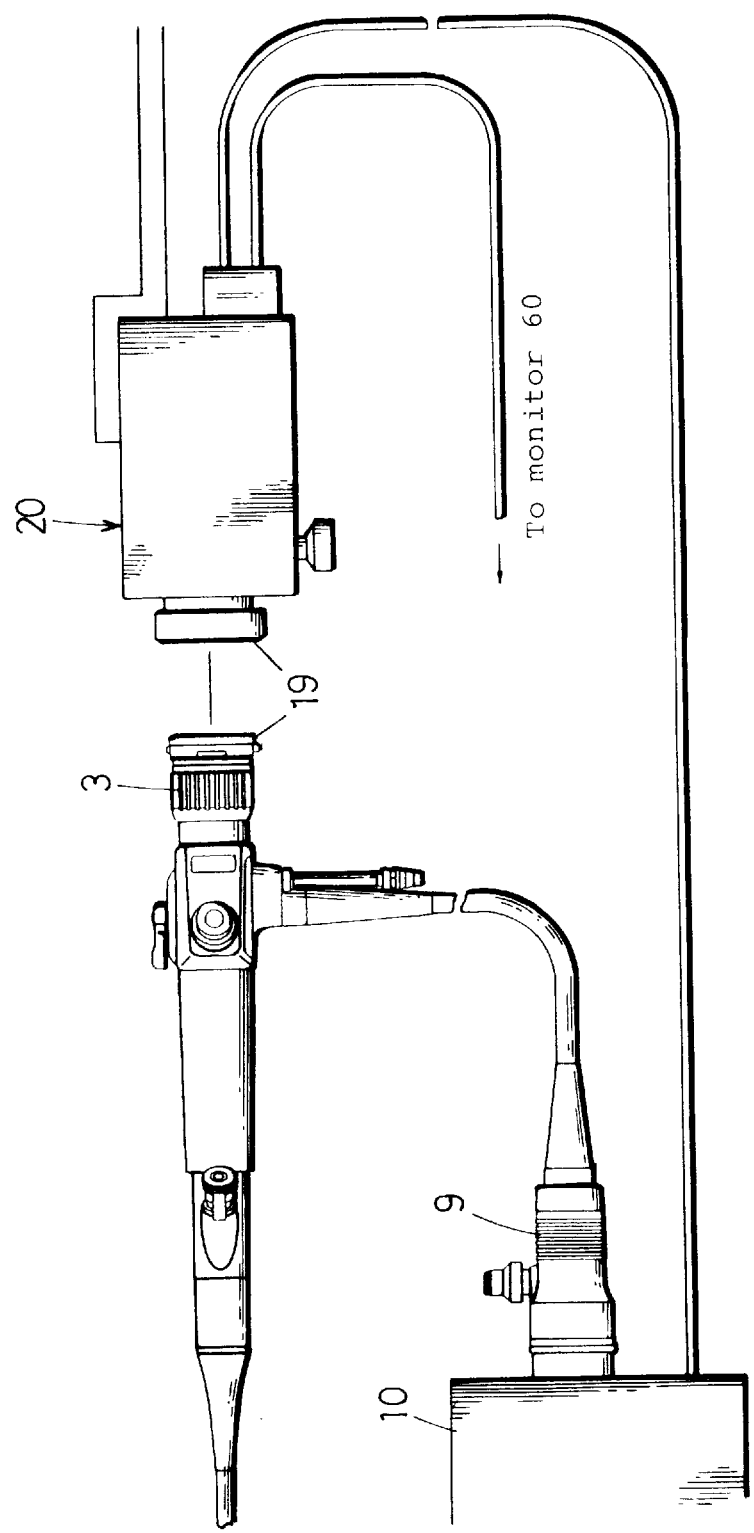
FIG. 3 shows the external appearance of the first embodiment of the present invention in a state where an endoscope and a television camera unit are disconnected from each other.

The eyepiece 3 is arranged so that the television camera unit 20 can be detachably and operatively connected thereto. FIGS. 1 and 2 show the system with the television camera unit 20 connected to the eyepiece 3, whereas FIG. 3 shows the system with the television camera unit 20 detached from the eyepiece 3.

A bayonet base-socket or other known mechanism for endoscope eyepiece attachment can be used as a mechanism 19 for detachably connecting the television camera unit 20 to the eyepiece 3. It is preferable to arrange the mechanism 19 so that the television camera unit 20 can be attached to the eyepiece 3 in such a manner as to be rotatable about the optical axis of the ocular optical system 6.

The television camera unit 20 contains an ordinary image pickup television camera 30 for taking an ordinary observation image passing through the ocular optical system 6, and a fluorescence image pickup television camera 40 for taking a fluorescence observation image passing through the ocular optical system 6.

The ordinary image pickup television camera 30 has a solid-state image sensing device 31 and an image-forming lens 32. Similarly, the fluorescence image pickup television camera 40 has a solid-state image sensing device 41 and an image-forming lens 42.

Accordingly, by attaching or detaching the television camera unit 20 to or from the eyepiece 3 of the endoscope, both the ordinary and fluorescence image pickup television cameras 30 and 40 are simultaneously attached to or detached from the eyepiece 3.

The fluorescence image pickup television camera 40 is equipped with an image intensifier 43 (I•I) for amplifying the intensity of light passing through the ocular optical system 6 by a considerable amount. An image-forming lens 44 is provided to form an observation image passing through the ocular optical system 6 on an entrance surface of the image intensifier 43.

A filter 45 for fluorescence observation is inserted in front of the image-forming lens 44. The fluorescence observation filter 45 does not pass light of wavelengths transmitted by the exciting light filter 12, but transmits only light of wavelengths longer than about 480 nanometers and shorter than about 520 nanometers Accordingly, only light of wavelengths longer than about 480 nanometers and shorter than about 520 nanometers can enter the image intensifier 43.

When a biological tissue is irradiated with light in a wavelength region of from 420 nanometers to 480 nanometers, a normal tissue is excited to generate fluorescent light in a wavelength region of the order of from about 480 nanometers to 600 nanometers, which has an intensity peak in a wavelength region of from about 480 nanometers to about 520 nanometers, whereas a cancerous tissue or other similarly affected tissue does not fluoresce.

Accordingly, when the exciting light filter 12 is inserted into the illuminating optical path, only fluorescent light generated by a normal tissue in the object enters the image intensifier 43 and is amplified.

A path switching optical system 50 is disposed inside the forward end of the television camera unit 20 in order to switch optical paths to allow light passing through the ocular optical system 6 to be selectively led to the image pickup surface of either of the two television cameras 30 and 40.

In this embodiment, a movable mirror 51 is used as the path switching optical system 50. The movable mirror 51 has a reflecting surface inclined at 45 degrees with respect to the optical axis of the ocular optical system 6 and is movable in a direction perpendicular to the optical axis of the ocular optical system 6. A cubic glass block 52 equalizes the optical path lengths between the exit end surface of the image guide fiber bundle 5 and the two solid-state image sensing devices 31 and 41. The cubic glass block 52 is cemented to the side of the movable mirror 51 so as to move together with the movable mirror 51.

A fixed mirror 53 is installed in front of the ordinary image pickup television camera 30, parallel to the movable mirror 51. The fixed mirror 53 has a reflecting surface facing the movable mirror 51 to receive an observation image reflected by the movable mirror 51 and to reflect the observation image to the image pickup surface of the ordinary image pickup television camera 30.

Consequently, when the movable mirror 51 lies on the optical axis of the ocular optical system 6, as shown in FIG. 1, an observation image passing through the ocular optical system 6 is reflected sidewardly by the movable mirror 51, further reflected by the fixed mirror 53 in a direction parallel to the optical axis of the ocular optical system 6, and formed on the surface of the solid-state image sensing device 31, of the ordinary image pickup television camera 30.

When the movable mirror 51 is moved sidewardly so as to withdraw from the optical axis of the ocular optical system 6, as shown in FIG. 2, an observation image passing through the ocular optical system 6 passes through the fluorescence observation filter 45 and is formed on the image-receiving surface of the image intensifier 43, in which the light intensity of the observation image is amplified. Then, the observation image is formed on the surface of the solid-state image sensing device 41 of the fluorescence image pickup television camera 40.

Referring to FIG. 1, there is a single monitor 60 in this embodiment. Thus, either of image signals from the ordinary and fluorescence image pickup television cameras 30 and 40 that is to be sent to the monitor 60 is selected by a line selector 61.

A control unit 70 contains a microprocessor and outputs control signals for controlling operations of the image intensifier 43, the line selector 61 and the exciting light filter 12 in response to the switching operation of the path switching optical system 50. A detector 71 detects a switching position of the path switching optical system 50 and sends a detection signal to the control unit 70.

The apparatus in this embodiment, arranged as described above, operates as follows: when ordinary observation is to be made, the exciting light filter 12 in the light source apparatus 10 is withdrawn from the illuminating light, path, as shown in FIG. 1. Thus, an object is illuminated with ordinary illuminating light, and an observation image of the object is taken by the ordinary image pickup television camera 30.

At the television camera unit 20, the power supply of the image intensifier 43 is turned off, and the line selector 61 is switched to the position for the ordinary image pickup television camera 30. Accordingly, an image signal output from the solid-state image sensing device 31 of the ordinary image pickup television camera 30 is sent to the monitor 60, and thus an ordinary observation image of light in the entire visible region is displayed on the monitor 60.

With the television camera unit 20 attached to the eyepiece 3, if the path switching optical system 50 is switched so that the movable mirror 51 is withdrawn sidewardly, as shown in FIG. 2, the exciting light filter 12 is inserted into the illuminating optical path in response to the switching operation of the path switching optical system 50. At the same time, the power supply of the image intensifier 43 is turned on, and the line selector 61 is switched to the position for the fluorescence image pickup television camera 40.

As a result, an object is illuminated with light in the wavelength region of from about 420 nanometers to about 480 nanometers that passes through the exciting light filter 12, and an observation image passes through the fluorescence observation filter 45 and enters the image intensifier 43.

Accordingly, only light of wavelengths longer than about 480 nanometers and shorter than about 520 nanometers that passes through the fluorescence observation filter 45 enters the image intensifier 43. Thus, only fluorescent light generated from the object enters the image intensifier 43, in which the intensity of the fluorescent light is amplified, and then a fluorescence observation image is taken by the solid-state image sensing device 41 of the fluorescence image pickup television camera 40 and displayed on the monitor 60.

It should be noted that the present invention is not necessarily limited to the above-described embodiment. For example, the path switching optical system 50 may be formed by using any type of optical system. However, the use of a reflecting optical system in which light is reflected twice so as to travel in a direction parallel to the previous optical axis, as shown in the first embodiment, enables the optical axes of the two television cameras 30 and 40 to be disposed parallel to each other; this is effective in reducing the size of the television camera unit 20.

Although in the foregoing embodiment the monitor 60 displays only an image selected by the line selector 61, it is possible to add other display control functions to the line selector 61. For example, the line selector 61 may be provided with a display control function whereby, in response to a switching operation of the path switching optical system 50, an image which has been taken and displayed since before the switching of the optical paths is displayed as a freeze image of small display screen area, and an image that is taken after the switching of the optical paths is simultaneously displayed as a dynamic image of large display screen area.

Figure 4:
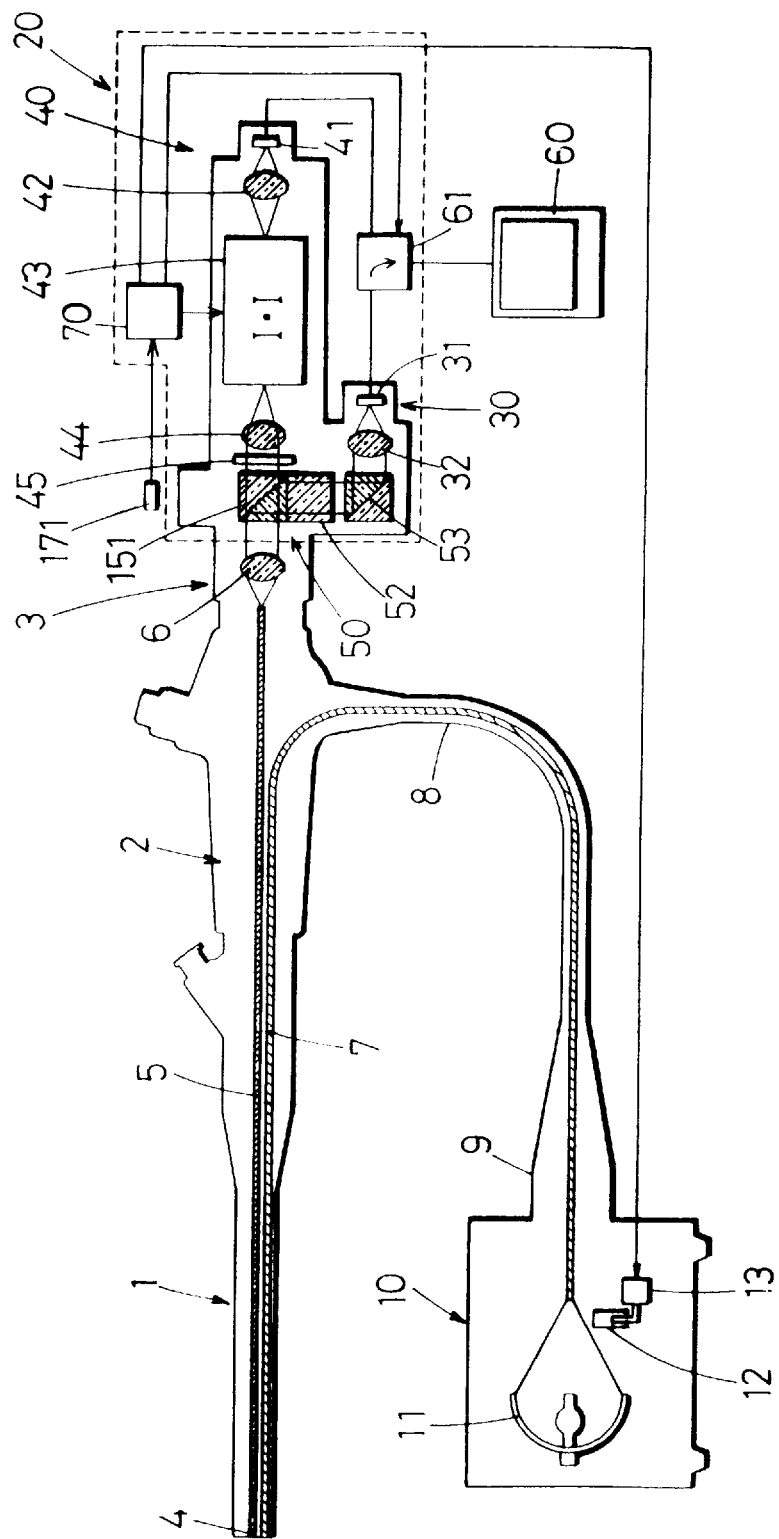
FIG. 4 shows the arrangement of a second embodiment of the present invention.

In another embodiment, as shown in FIG. 4, the movable mirror 51 in FIG. 1 may be replaced by a beam splitter (light-dividing device) 151 having no wavelength selectivity. In this embodiment, the beam splitter is immovably installed. In the fluorescence observation mode, an observation image is taken with both the ordinary image pickup television camera 30 and the fluorescence image pickup television camera 40, and images obtained by the two television cameras 30 and 40 are simultaneously displayed on the monitor 60.

In this case, the ordinary image pickup television camera 30 forms not a full-color image but a blue image of the object illuminated with light (exciting light) in the wavelength region of from about 420 nanometers to about 480 nanometers passing through the exciting light filter 12. However, this image can be used as a reference image for confirming the position of the region under observation. It should be noted that the display of the reference image on the monitor 60 may be changed to monochromatic display.

In this embodiment, when an ordinary image is to be taken, the power supply of the image intensifier 43 is turned off by operating a change-over switch 171, and the line selector 61 is switched to the position for the ordinary image pickup television camera 30, in the same way as in the embodiment shown in FIG. 1, Further, the exciting light filter 12 is withdrawn from the illuminating optical path. Thus, an object is illuminated with ordinary illuminating light, and an observation image of the object is taken by the ordinary image pickup television camera 30.

Figure 5:
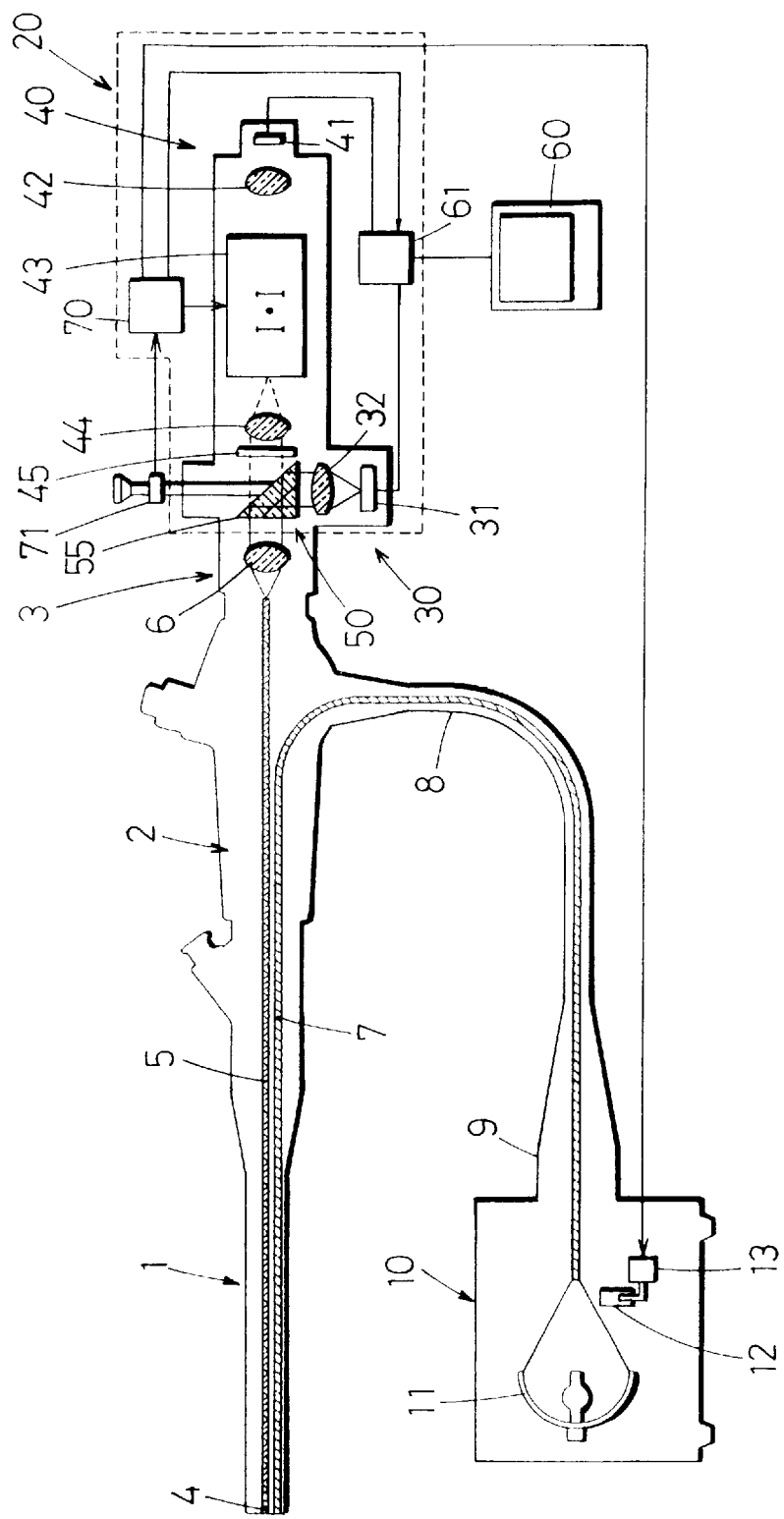
FIG. 5 shows the arrangement of a third embodiment of the present invention in an ordinary observation mode, in which a roof-type reflecting member is used.

FIG. 5 shows another embodiment in which a roof prism 55 functions as a roof-type reflecting member that reflects an image in such a manner that the right and left portions of the image are not interchanged so as to be capable of being selectively inserted into and withdrawn from the optical path of light passing through the ocular optical system 6 as the path switching optical system 50 for selectively leading light passing through the ocular optical system 6 to the image pickup surface of either of the two television cameras 30 and 40.

In this embodiment, the ordinary image pickup television camera 30 is disposed at right angles to the fluorescence image pickup television camera 40, and the solid-state image sensing device 31 is disposed so that the orientation of its image pickup surface is conformable to the orientation of the image that is rotated by the action of the roof prism 55.

Therefore, an image signal that is output from the solid-state image sensing device 31 during the ordinary observation mode is similar to that obtained from the solid-state image sensing device 31 in the first embodiment, shown in FIG. 1. The other portions are the same as those of the first embodiment.

According to the present invention, an ordinary image pickup television camera and a fluorescence image pickup television camera are provided integrally with each other so that the two television cameras can be simultaneously attached to the eyepiece of an endoscope. Accordingly, the television cameras need not be attached to or detached from the endoscope when the ordinary observation mode and the fluorescence observation mode are switched over from one to the other. Therefore, endoscopy can be smoothly carried out.

By arranging the apparatus so that the operations of each part of the apparatus for ordinary observation and fluorescence observation automatically change over from one to the other in response to change of the observation modes, the apparatus can be used considerably easily.

While the invention has been described by reference to specific embodiments chosen for purposes of illustration, it should be apparent that numerous modifications could be made thereto by those skilled in the art without departing from the basic concept and scope of the invention.

What is claimed is:

1. A biological fluorescence diagnostic apparatus having a system that irradiates biological tissue with illuminating light from a light source having a wavelength range within which the biological tissue generates fluorescent light upon light irradiation and that transmits an image through an ocular optical system provided in an eyepiece of an endoscope, said apparatus comprising:

a television camera unit including an ordinary image pickup television camera for taking an ordinary endoscopic observation image passing through the ocular optical system of the endoscope, and a fluorescence image pickup television camera with an image intensifier for taking a fluorescence observation image passing through the ocular optical system of the endoscope after amplifying a light intensity of said fluorescence observation image, said ordinary image pickup television camera and said fluorescence image pickup television camera being distinct and being integrally mountable to the eyepiece of the endoscope;

a path switching optical system including a reflecting surface, said path switching optical system mounted to be selectively inserted into and withdrawn from an optical path of light passing through the ocular optical system;

a filter selectively insertable into and movable out of an illuminating light path of the endoscope, said filter transmitting light having a wavelength range within which the biological tissue generates fluorescent light;

a control unit;

a detector that detects a position of said path switching optical system, said control unit controlling said image intensifier and said filter in response to an output of said detector; and a system that operatively connects said television camera unit to the eyepiece of the endoscope.

2. A biological fluorescence diagnostic apparatus according to claim 1, said path switching optical system selectively transmitting light passing through the ocular optical system of the endoscope to an image pickup surface of either of said two television cameras.

3. A biological fluorescence diagnostic apparatus according to claim 2, said path switching optical system further comprising a reflecting optical system in which light passing through the ocular optical system along a first optical axis is reflected twice so as to travel in a direction having a second optical axis parallel to the first optical axis, whereby the optical axes of said two television cameras are disposed parallel to each other.

4. A biological fluorescence diagnostic apparatus according to claim 2, wherein said path switching optical system comprises a roof-type reflecting member capable of being selectively inserted into and withdrawn from an optical path of light passing through the ocular optical system of the endoscope, wherein said roof-type reflecting member reflects an image such that right and left portions of said image are not interchanged.

5. A biological fluorescence diagnostic apparatus according to claim 2, further comprising a line selector for selectively delivering an image signal from either of said two television cameras to a monitor.

6. A biological fluorescence diagnostic apparatus according to claim 5, wherein said line selector selectively switches the image signal delivered to the monitor in response to selective insertion or withdrawal of said path switching optical system from the optical path of light passing through the ocular optical system of the endoscope.

7. A biological fluorescence diagnostic apparatus according to claim 2, wherein the light source includes an exciting light irradiating means having an exciting light filter which transmits only light having a wavelength range within which the biological tissue generates fluorescent light upon light irradiation, said biological fluorescence diagnostic apparatus including a system that selectively moves the exciting light filter into and out of an illuminating light path of the endoscope.

8. A biological fluorescence diagnostic apparatus according to claim 7, wherein said exciting light filter transmits only light in a wavelength region of from 420 nanometers to about 480 nanometers.

9. A biological fluorescence diagnostic apparatus according to claim 7, wherein the exciting light filter is selectively moved into and out of the light path of the endoscope by said selective moving system in response to insertion and withdrawal of said path switching optical system to and from the optical path.

10. A biological fluorescence diagnostic apparatus according to claim 7, wherein said fluorescence image pickup television camera includes a fluorescence observation filter which does not transmit light of wavelengths transmitted by the exciting light filter of the endoscope, but transmits light in at least a part of the wavelength range in which fluorescent light is generated by the biological tissue.

11. A biological fluorescence diagnostic apparatus according to claim 10, wherein said fluorescence observation filter transmits only light of wavelengths longer than about 480 nanometers and shorter than about 520 nanometers.

12. The biological fluorescence diagnostic apparatus according to claim 1, wherein said system that operatively connects, detachably and operatively connects said television camera unit to the eyepiece of the endoscope.

13. A biological fluorescence diagnostic apparatus including an irradiating mechanism for irradiating a biological tissue with light from a light source having a wavelength range within which the biological tissue generates fluorescent light, the light transmitted through an ocular optical system provided in an eyepiece of an endoscope, said apparatus comprising:

a camera unit including a first camera that provides an ordinary endoscopic observation image that passes through the ocular optical system of the endoscope and a second camera that provides a fluorescence observation image passing through the ocular optical system of the endoscope, said second camera including an image intensifier that amplifies a light intensity of the fluorescence observation image, said first camera and said second camera being integrally mountable to the eyepiece of the endoscope;

an optical system including a reflecting surface, said optical system mounted to be selectively inserted into and withdrawn from an optical path of light passing through the ocular optical system;

a filter selectively insertable into and movable out of a light path of the endoscope, said filter transmitting light having a wavelength range within which the biological tissue generates fluorescent light;

a control unit;

a detector that detects a position of said optical system, said control unit controlling said image intensifier and said filter in response to an output of said detector; and a system that operatively connects said camera unit, comprising said first camera and said second camera to the eyepiece of the endoscope.

14. The biological fluorescence diagnostic apparatus according to claim 13, said optical system selectively directing light to an image pickup surface of either of said first camera or said second camera.

15. The biological fluorescence diagnostic apparatus according to claim 13, said optical system comprising a roof type reflecting member mounted for selective insertion into and withdrawal from an optical path of light passing through the ocular optical system of the endoscope, said roof type reflecting member reflecting an image without reversing right and left portions of the image.

16. The biological fluorescence diagnostic apparatus according to claim 13, further comprising a line selector that selectively delivers an image signal from either of said cameras to a monitor.

17. The biological fluorescence diagnostic apparatus according to claim 16, said line selector selectively switching the image signal delivered to the monitor in response to selective insertion or withdrawal of said optical system from the optical path of light passing through the ocular optical system of the endoscope.

* * * * *